United States Patent [19]
Jacobsen et al.

[11] Patent Number: 5,911,717
[45] Date of Patent: Jun. 15, 1999

[54] CATHETER DELIVERABLE THROMBOGENIC APPARATUS AND METHOD

[75] Inventors: Stephen C. Jacobsen; Clark C. Davis, both of Salt Lake City; John A. Lippert, Park City, all of Utah

[73] Assignee: Precision Vascular Systems, Inc., Salt Lake City, Utah

[21] Appl. No.: 08/819,611

[22] Filed: Mar. 17, 1997

[51] Int. Cl.⁶ ..................................................... A61B 17/00
[52] U.S. Cl. .............................. 606/1; 606/151; 606/200
[58] Field of Search .................... 606/1, 108, 151, 606/191–200

[56] References Cited

U.S. PATENT DOCUMENTS

| | | | |
|---|---|---|---|
| 4,994,069 | 2/1991 | Ritchart et al. | |
| 5,437,288 | 8/1995 | Schwartz et al. | 600/585 |
| 5,476,472 | 12/1995 | Dormandy et al. | 606/108 |
| 5,645,558 | 7/1997 | Horton | 606/198 |
| 5,649,949 | 7/1997 | Wallace et al. | 606/198 |
| 5,658,308 | 8/1997 | Snyder | 606/198 |

*Primary Examiner*—Glenn K. Dawson
*Attorney, Agent, or Firm*—Thorpe North & Western, LLP

[57] ABSTRACT

A catheter deliverable thrombogenic device includes a catheter for threading into a body vasculature passageway to a target location, and a resilient wire element coiled and shaped to occupy a certain volume when unconstrained, and to straighten when inserted lengthwise into and constrained by the catheter, for ultimate discharge therefrom to expand and occupy the target location. The wire element includes a plurality of cuts on the exterior surface thereof at selected locations to increase the flexibility of the wire element.

20 Claims, 1 Drawing Sheet

CATHETER DELIVERABLE THROMBOGENIC APPARATUS AND METHOD

BACKGROUND OF THE INVENTION

This invention relates to vaso-occlusive devices for arresting blood flow in body vasculature or cavities.

Devices which occlude blood flow and/or initiate blood clotting, and which can be introduced into the body via a catheter or other cannula are valuable for stopping bleeding or the threat of bleeding, cutting off blood supply to a diseased organ, reducing blood flow to an organ, rebuilding a defective organ, etc. Devices typically utilized are coils or particles which are deployed through a catheter to a target site where arresting blood flow is desired. In addition, various solutions may be delivered through the catheter either for assisting and accelerating clotting or in treating the medical problem.

Typical devices used in the past include platinum coils which were inserted into the catheters and then pushed therethrough to the target site using a conventional catheter guide wire or other device as a "plunger". The coil devices are preset in a desire shape, typically a simple helix, so that after they are delivered to the desired site, they resume their original shape. Prior art platinum coil devices have often been ineffective in holding their positions at the delivered site, and thus ineffective in occluding at the site.

Types of particles used in the past for occluding blood flow include PVA or hydrophilic particles that swell to a larger size when blood is absorbed. This swelling, of course, aids in stopping the flow of blood, assuming the positions of the particles are maintained.

The prior art approaches for arresting blood flow are fairly rudimentary and only partially successful in achieving the desired blood flow stoppage.

SUMMARY OF THE INVENTION

It is an object of the invention to provide new and improved vaso-occlusive devices which may be easily deployed to a target site in the human body and which are effective in inducing clotting or otherwise arresting blood flow.

It is also an object of the invention to provide such devices which are easily manufactured and which can be tailor-made in size and configuration to accommodate the targeted deployment location.

It is a further object of the invention to provide such devices which may be quickly and easily deployed to a target location in the body, and remain in place.

The above and other objects of the invention are realized in a specific illustrative embodiment of a thrombogenic apparatus which includes a catheter for threading into a body vasculature passageway to a target location, and a wire element coiled and shaped to occupy a certain volume when unconstrained, and to straighten when inserted lengthwise into and constrained by the catheter, for ultimate discharge therefrom to expand and occupy the target location.

In accordance with one aspect of the invention, the wire element is formed to have a coil diameter which becomes gradually smaller toward a distal end. In accordance with another aspect of the invention, the smaller diameter coils near and at the distal end are tightly wound to inhibit flow of blood therepast, when inserted into a blood vessel.

The wire element may be a single solid wire or a tubular wire.

To control flexibility and "holding strength" of the wire element in a vessel, especially at the distal end, cuts may be formed on the exterior of the wire element and spaced—and width—and depth-controlled to achieve the flexibility and shape desired.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1A:
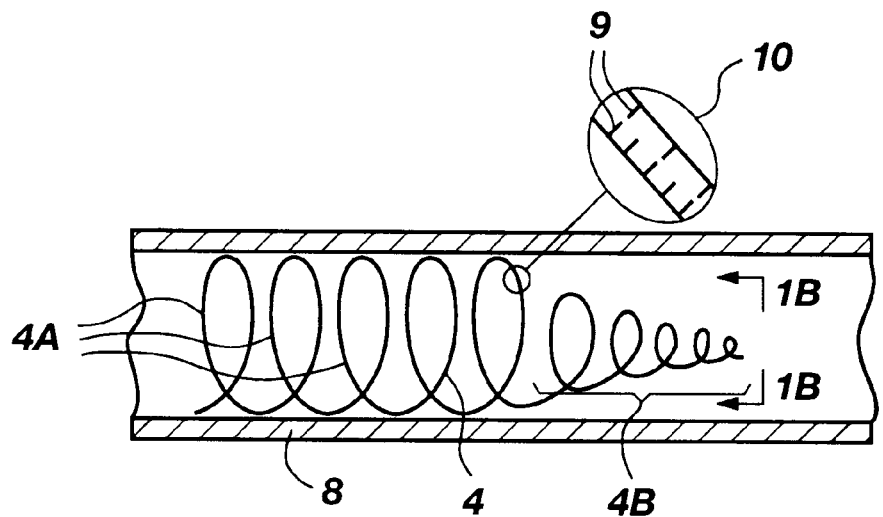
FIG. 1A is a side, fragmented, cross-sectional view of a thrombogenic, coiled-wire device made in accordance with the principles of the present invention.
Figure 1B:
FIG. 1B is a front end view of the wire coil of FIG. 1A, taken along lines 1B—1B.

Referring to FIG. 1A and 1B, there is shown a side, cross-sectional, fragmented view and an end view respectively of a resilient wire 4 which has been formed into a coil. In FIG. 1A, the wire 4 is shown disposed in a blood vessel 8. The wire 4 includes a larger diameter section 4a and a gradually narrowing section 4b. The coils in the larger diameter section 4a expand to contact the walls of the blood vessel 8 to hold the coil wire 4 in place. The narrower diameter section 4b serves as the leading or distal end of the coil wire 4 and preferably is more flexible to minimize damage or trauma to vessel walls when inserting the coil wire (to be discussed momentarily).

The flexibility and shape of the coil wire 4 may be controlled by appropriate placement of cuts 9 on the exterior surface (such as shown at 10 in enlarged view in FIG. 1) and described in more detail in co-pending patent application Ser. No. 08/568,490, filed Dec. 7, 1995, and incorporated herein by reference. By appropriate spacing of the cuts both circumferentially and longitudinally and by varying the depth and width of the cuts, desired flexibility and shape can be achieved. For example, generally spacing the cuts closer together and making them wider and deeper provides greater flexibility and vice versa. Cuts in the wire 4 also enhance the wire's thrombogenicity, and provide sites for holding clotting agents or other drugs to be deposited in the blood vessel.

The wire 4 might, for example, be formed of a highly elastic nickel-titanium alloy wire with directionally specific cuts and having an outside diameter of about 0.008 inch to 0.060 inch. The diameter of the larger diameter section 4a advantageously is from about 3 to 12 mm whereas the diameter of the smallest diameter coil in section 4b advantageously is from about 1 to 2 mm, both calculated when the coil wire 4 is unconstrained.

Tapering the diameter of the wire coil 4 as in section 4b provides a greater barrier and density (of occlusion wires) to the flow of blood, and thus greater ability to occlude, as best seen in the FIG. 1B view, taken along lines 1B—1B of FIG. 1A. (Controlling the tapering of [and spacing between] coils allows use of the coil as a limited leak valve or a complete block.

The coil wire 4 may either be a solid wire or a tubular wire, of the general dimensions discussed above. If tubular, and formed with cuts on the exterior surface, some of those cuts could be made to extend through the tubular walls to the interior and then medication placed in the hollow of the tube to gradually leak from the cuts after the coil wire were put in position at the target site. In this manner, the thrombogenic function of the coil wire 4 is augmented by a medication delivery function. Also, thrombogenic fibers could be disposed in the hollow of a tubular wire to enhance occlusion and clotting.

Figure 2:
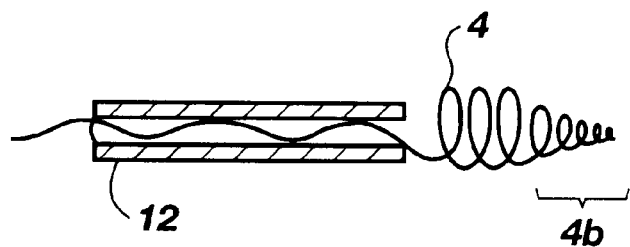
FIG. 2 is a side, fragmented, cross-sectional view of a coil-wire device made in accordance with the principles of the present invention, shown partially disposed in a catheter.

FIG. 2 shows a side, fragmented, cross-sectional view of a wire coil 4 partially disposed in a catheter 12. For deployment of the coil wire 4 to a target location in a vasculature passageway or other cavity in the body, the wire 4 may be threaded into the catheter 12 generally straight as shown in FIG. 2, and then pushed through the catheter by another guide wire (not shown) or similar device which serves as a type of plunger to force the coil wire out the distal end of the catheter where it then expands to seat itself at the target location. When deployed to a target site in the body past which blood is flowing, the wire coil 4 serves to slow the flow to allow for coagulation or clotting and ultimately the arresting of further flow. To aid in the clotting process, clotting agents, in the form of a solution, might be delivered through the catheter 12 along with the deployment of the coil wire 4, to the target site. Alternatively, such solution could be disposed in a tubular wire coil 4 to gradually leak from the tube through side cuts which extend through the tubular walls, as previously discussed above.

The embodiment of the wire coil 4 shown in FIG. 2 includes a narrowed distal section 4b in which the coils are tightly wound to the extent that the adjacent coils touch. With such high density packing of the coils, the flow of blood is substantially stopped even before coagulation or clotting takes place.

Figure 3:
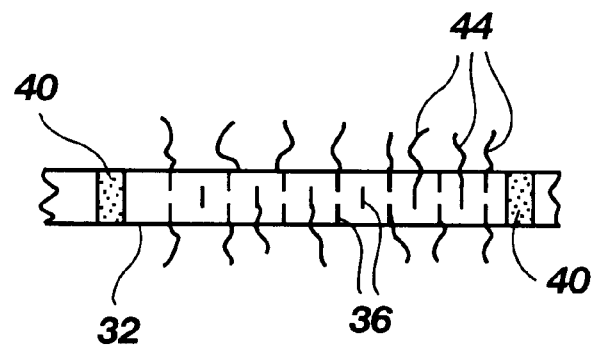
FIG. 3 is a side, fragmented view of still another embodiment of a coiled-wire device made in accordance with the principles of the present invention.

FIG. 3 shows a side, fragmented view of a wire 32 having cuts 36 formed in the exterior surface thereof. The wire 32 could be either solid or tubular, and would be formed into a coil having a tapered distal end, such as shown in FIG. 1A. The cuts 36 would be placed, as earlier described, to control the flexibility and shape along the length of the wire. These cuts could be formed either by saw cutting or three-dimensional etching such as described in U.S. Pat. No. 5,106,455.

Radiopaque bands 40 may be wrapped about the wire 32 at predetermined locations along the length thereof to allow tracking movement of the wire in a vasculature passageway in the body. Thrombogenic fibers 44 made, for example, of Dacron® or other polymers are attached to the wire 32 at certain locations, preferably where cuts have been made. The fibers 44 could be tied into the wire 32, attached by an adhesive, fused or other well-known bonding method. These fibers promote the clotting and coagulation of blood flowing past the wire 32 which, of course, is the desired result.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Thrombogenic apparatus comprising
   a catheter for threading into a body vasculature passageway to a target location, and
   a resilient wire means shaped to occupy a certain volume when unconstrained, and to straighten when inserted lengthwise into and constrained by the catheter, for ultimate discharge therefrom to expand and occupy the target location, said wire means formed into a coil and including a plurality of cuts on the exterior surface thereof at selected locations, to increase the flexibility of the wire means.

2. An apparatus as in claim 1 wherein said coil has a diameter which becomes gradually smaller toward a distal end.

3. An apparatus as in claim 2 wherein the smaller diameter coils near and at the distal end are tightly wound to inhibit flow of blood therepast, when inserted into a blood vessel.

4. An apparatus as in claim 2 wherein the coil diameter at a proximal end is from about 3 to 12 millimeters, and wherein the coil diameter at the distal end is from about 1 to 3 millimeters.

5. An apparatus as in claim 1 wherein said wire includes more cuts per unit length near the distal end than at other locations, such that the distal end is more flexible.

6. An apparatus as in claim 1 further comprising lengths of fiber disposed in the cuts to extend outwardly of the wire to assist in thrombosis.

7. An apparatus as in claim 6 wherein the fibers are made of material selected from the group consisting of dacron and silk.

8. An apparatus as in claim 1 wherein said wire is solid.

9. An apparatus as in claim 1 wherein said wire means is made of an alloy of nickel and titanium.

10. An apparatus as in claim 9 wherein said wire means has a diameter of from about 0.008 to 0.060 inches.

11. A thrombogenic apparatus comprising
    a catheter for threading into a body vasculature passageway to a target location, and
    a resilient, tubular wire having sidewalls surrounding a central hollow shaped to occupy a certain volume when unconstrained, and to straighten when inserted lengthwise into and constrained by the catheter, for ultimate discharge therefrom to expand and occupy the target location, said resilient, tubular wire including a plurality of cuts on the exterior surface thereof at selected locations, to increase the flexibility of said wire.

12. An apparatus as in claim 11 wherein at least some of said cuts extend through the sidewalls to the central hollow.

13. An apparatus as in claim 12 further including medication disposed in the central hollow for leaking therefrom through the cuts which extend through the sidewalls, when the apparatus is placed at the target location.

14. An apparatus as in claim 11 further including fiber disposed in the hollow of the wire to assist in thrombosis.

15. Thrombogenic apparatus comprising
    a catheter for threading into a body vasculature passageway to a target location, and
    a resilient wire coiled and shaped to occupy a certain volume when unconstrained, and to straighten when inserted lengthwise into and constrained by the catheter, for discharge therefrom to expand and occupy the target location, said wire formed to have a coil diameter which becomes gradually smaller toward a distal end and having a plurality of cuts on an exterior surface thereof.

16. Apparatus as in claim 15 wherein the smaller diameter coils near and at the distal end are tightly wound to inhibit flow of blood therepast when inserted into a blood vessel.

17. Apparatus as in claim 15 wherein said wire is solid.

18. Apparatus as in claim 15 wherein said wire is tubular having sidewalls surrounding a central hollow.

19. Apparatus as in claim 18 wherein at least some of said plurality of cuts extend through the sidewalls to the central hollow.

20. Apparatus as in claim 19 further including medication disposed in the central hollow for leaking therefrom through the cuts which extend through the sidewalls, when the apparatus is placed at the target location.

* * * * *